(12) United States Patent
Cheng et al.

(10) Patent No.: US 11,109,763 B2
(45) Date of Patent: Sep. 7, 2021

(54) PHOTOACOUSTIC CATHETER AND IMAGING SYSTEM USING SAME

(71) Applicant: PURDUE RESEARCH FOUNDATION, West Lafayette, IN (US)

(72) Inventors: Ji-xin Cheng, West Lafayette, IN (US); Pu Wang, West Lafayette, IN (US); Yingchun Cao, West Lafayette, IN (US); Jie Hui, West Lafayette, IN (US)

( * ) Notice: Subject to any disclaimer, the term of this patent is extended or adjusted under 35 U.S.C. 154(b) by 358 days.

(21) Appl. No.: 15/998,889

(22) PCT Filed: Feb. 13, 2017

(86) PCT No.: PCT/US2017/017598
§ 371 (c)(1),
(2) Date: Aug. 15, 2018

(87) PCT Pub. No.: WO2017/139728
PCT Pub. Date: Aug. 17, 2017

(65) Prior Publication Data
US 2019/0216330 A1   Jul. 18, 2019

Related U.S. Application Data

(60) Provisional application No. 62/295,033, filed on Feb. 13, 2016.

(51) Int. Cl.
*A61B 5/00* (2006.01)
*A61B 8/00* (2006.01)
(Continued)

(52) U.S. Cl.
CPC ........ *A61B 5/0095* (2013.01); *A61B 5/02007* (2013.01); *A61B 8/12* (2013.01);
(Continued)

(58) Field of Classification Search
CPC ....... A61B 8/0891; A61B 8/12; A61B 8/4416; A61B 8/445; A61B 8/5246–5261;
(Continued)

(56) References Cited

U.S. PATENT DOCUMENTS

| | | | |
|---|---|---|---|
| 2007/0093702 A1* | 4/2007 | Yu | A61B 5/14552 600/326 |
| 2008/0097217 A1* | 4/2008 | Itoh | A61B 5/6848 600/459 |

(Continued)

FOREIGN PATENT DOCUMENTS

KR    101440109 B1 *  9/2014   ............. A61B 8/085

OTHER PUBLICATIONS

Wei, Wei, et al. "Integrated ultrasound and photoacoustic probe for co-registered intravascular imaging." Journal of biomedical optics 16.10 (2011): 106001. (Year: 2011).*

(Continued)

*Primary Examiner* — Sean D Mattson
(74) *Attorney, Agent, or Firm* — Tyler B. Droste; Gutwein Law

(57) ABSTRACT

A photoacoustic catheter includes an elongated catheter body and a housing positioned near a distal end of the elongated catheter body. A length of multimode fiber extends through the elongated catheter body and has a distal end that is beveled at about 45° relative to a longitudinal axis of the multimode fiber and is positioned in the housing. An ultrasonic transducer, electrically connected to an electrical wire extending along the elongated catheter body, is positioned within the housing. A mirror element is also positioned within the housing and includes a mirror surface beveled at about 45° relative to the longitudinal axis of the multimode fiber. The catheter is operable to deliver an optical wave through the multimode fiber and to deliver an ultrasonic (Continued)

wave collinearly from the housing and out of an aperture of the housing to obtain optical data and ultrasonic data within a mammalian luminal organ.

19 Claims, 10 Drawing Sheets

(51) Int. Cl.
    *A61B 5/02*     (2006.01)
    *A61B 8/12*     (2006.01)
    *A61M 25/00*     (2006.01)

(52) U.S. Cl.
    CPC ............ *A61B 8/445* (2013.01); *A61B 5/0066* (2013.01); *A61B 2560/0233* (2013.01); *A61M 25/0067* (2013.01)

(58) Field of Classification Search
    CPC ........ A61B 5/0093–0095; A61B 5/489; A61B 5/6852; A61B 5/02007; A61B 5/0066; A61B 2560/0233; A61M 25/0067; G01S 15/8965; G01N 29/243; G01N 29/2418; G01N 21/1702; G01N 2201/067; G01N 2201/106
    See application file for complete search history.

(56) References Cited

U.S. PATENT DOCUMENTS

| | | | |
|---|---|---|---|
| 2008/0177183 A1* | 7/2008 | Courtney | A61B 5/0035 600/463 |
| 2011/0098572 A1* | 4/2011 | Chen | A61B 5/0066 600/463 |
| 2011/0275890 A1* | 11/2011 | Wang | A61B 8/12 600/104 |
| 2013/0338478 A1* | 12/2013 | Hi Rota | A61B 5/0095 600/407 |
| 2013/0338498 A1* | 12/2013 | Emelianov | A61B 8/12 600/431 |

OTHER PUBLICATIONS

Karpiouk, Andrei B., et al. "Feasibility of in vivo intravascular photoacoustic imaging using integrated ultrasound and photoacoustic imaging catheter." Journal of biomedical optics 17.9 (2012): 096008. (Year: 2012).*

\* cited by examiner

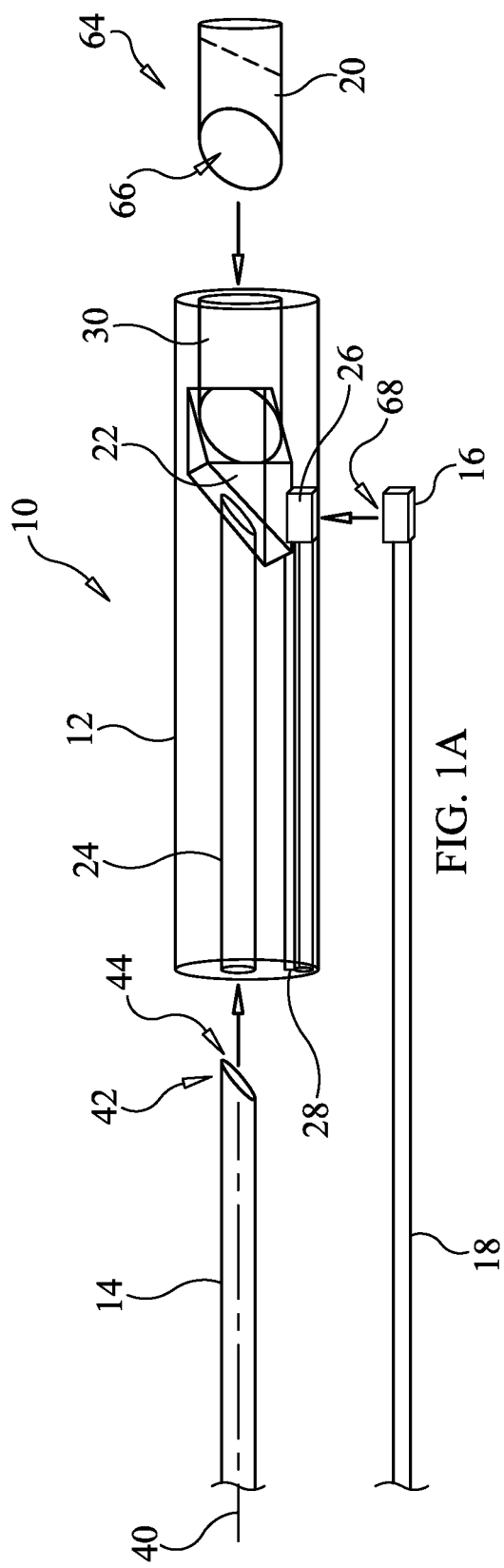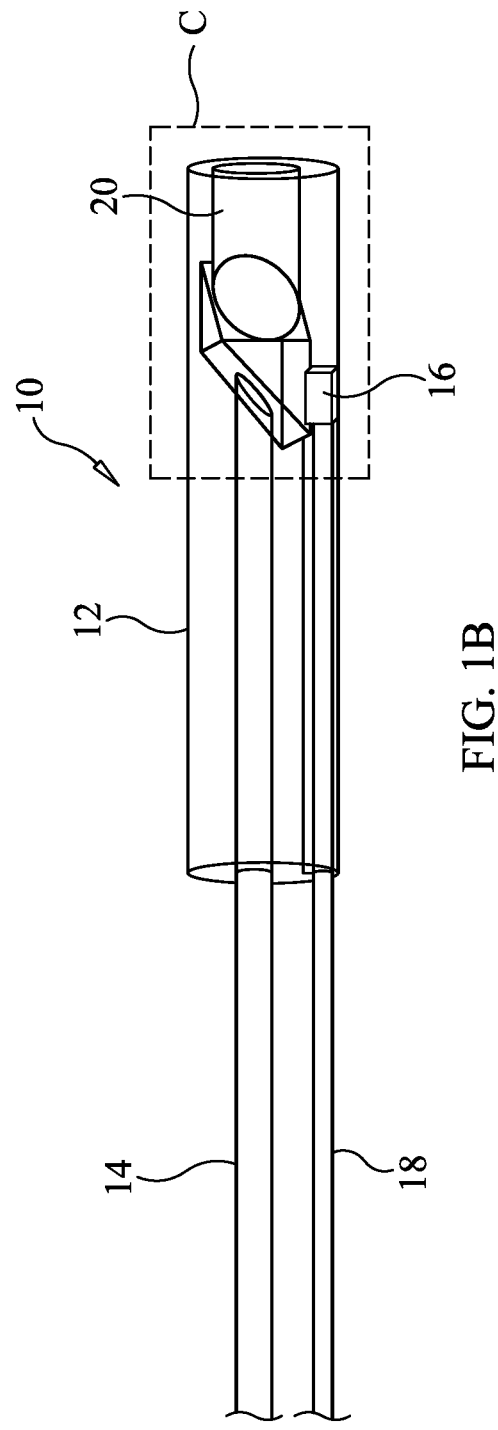
FIG. 1A
FIG. 1B ant_id="msg_01Eoh" -->

PHOTOACOUSTIC CATHETER AND IMAGING SYSTEM USING SAME

CROSS-REFERENCE TO RELATED APPLICATION

This U.S. Patent Application claims priority to U.S. Provisional Application: 62/295,033 filed Feb. 13, 2016, the disclosure of which is considered part of the disclosure of this application and is hereby incorporated by reference in its entirety.

GOVERNMENT RIGHTS

This invention was made with government support under HL125385 awarded by the National Institutes of Health. The government has certain rights in the invention.

FIELD OF THE INVENTION

The present application relates to a photoacoustic catheter, and more particularly to a photoacoustic catheter incorporating collinear alignment of optical and acoustic waves.

BACKGROUND

This section introduces aspects that may help facilitate a better understanding of the disclosure. Accordingly, these statements are to be read in this light and are not to be understood as admissions about what is or is not prior art.

Cardiovascular disease has been the leading cause of death in the United States and many other developed countries over the past century. Atherosclerosis, a major form of cardiovascular disease, is caused by the chronic accumulation of lipids and fibrous elements within the wall of an artery. This plaque can grow and become clinically symptomatic if it significantly encroaches and obstructs the lumen of the artery. A plaque may also rupture and result in acute coronary syndrome or even sudden death. Therefore, the early detection of plaques that are vulnerable for rupture is essential in the diagnosis, treatment, and prevention of cardiovascular diseases. Non-invasive modalities such as X-ray angiography, magnetic resonance, and computed tomography angiography have been used to visualize obstructive stenosis in coronary arteries. However, vulnerable plaques prone to rupture are often non-obstructive or moderately obstructive, thus evading detection by these modalities. Intravascular ultrasound (IVUS) can provide important morphologic information of arteries including lumen geometry, plaque burden, and vessel structure. However, the sensitivity and specificity for differentiation of plaque composition is limited, partly due to the lack of chemical contrast with IVUS. Intravascular optical coherence tomography has been reported, but these optical imaging modalities fail to provide necessary imaging depth and chemical specificity for vulnerable plaque detection. Near-infrared spectroscopy provides chemical selectivity, but it lacks the spatial resolution to define the lipid core size and its detection sensitivity is compromised by scattered photons.

Catheter-based intravascular photoacoustic (IVPA) imaging, on the basis of converting the overtone vibrational absorption in an arterial tissue into thermoelastic waves detectable with an ultrasonic transducer, is an emerging modality with potential of bridging the aforementioned gaps. IVPA imaging offers the following advantages. First, the optical absorption-induced contrast provides a unique approach to differentiate chemical composition of arteries. Second, the imaging depth of IVPA is extended beyond the ballistic regime owing to the diffused photon absorption and 2-3 orders of magnitude lower acoustic scattering in tissues compared to optical scattering. Third, by sharing the same detector, IVUS is inherently compatible with IVPA imaging. Such a hybrid modality provides complementary information of the tissue.

The desirable characteristics of a clinically feasible IVPA catheter include having a small diameter, being flexible, and being capable of imaging through blood and of acquiring images with high sensitivity and chemical specificity at an acceptable frame rate. These requirements collectively render the design and fabrication of a high-performance IVPA probe to be one of the most challenging tasks in the photoacoustic imaging field. A number of groups have reported IVPA catheters with diameters approaching the clinical target of about 1 millimeter (mm). Specifically, the Emelianov group reported two designs of IVPA catheters, one based on side fire fiber and the other based on mirror reflection. Both designs were based on a front-to-back arrangement of the light delivery element and ultrasonic transducer. The Chen group introduced another design of an IVPA catheter based on parallel arrangement of side-firing fiber and transducer, where two different frequencies, 35 MHz and 80 MHz, of the transducer were performed to demonstrate an outstanding axial resolution of 35 microns ($\mu$m). The Xing group introduced an intravascular confocal photoacoustic probe with a dual-element ultrasound transducer. The Song group reduced the diameter of an IVPA catheter probe to 1.1 mm by carefully arranging the positions of the optical and acoustic elements. Most recently, the inventors further reduced the probe diameter of a conventional IVPA catheter to 0.9 mm.

Despite these advances, sufficient arterial imaging depth has not been shown for these single-element transducer-based IVPA catheters, largely because the optical and ultrasonic waves were cross-overlapped in a very limited space. Although the overlap range can be altered by changing the coupling angle, it is hard to maintain the photoacoustic sensitivity constant along the millimeter-scale imaging depth. Furthermore, the IVUS and IVPA images in these non-collinear designs are not truly co-registered along the imaging depth, which may lead to poor localization of artery and plaque features. Further, assembly of such non-collinear designs is not trivial, as all the components must be constrained to a limited space. To maximize the overlap of an incident optical field and generated acoustic wave, the inventors recently demonstrated a coaxial design based on a ring-shaped transducer. However, at 2.9 mm, the outer diameter of the probe needed to be further reduced for clinical compatibility. Accordingly, there remains a need for further contributions in this area of technology.

BRIEF SUMMARY OF THE INVENTION

At least one exemplary embodiment of the present disclosure includes a photoacoustic catheter, including an elongated catheter body having a lumen defined therethrough and a housing positioned at or near a distal end of the elongated catheter body, the housing defining an aperture therethrough, a length of multimode fiber extending through at least part of the lumen of the elongated catheter body, the multimode fiber having an axis along its length, whereby a distal end of the multimode fiber is beveled at or about 45° to the axis and is located within the housing, an electrical wire extending along the elongated catheter body, an ultrasonic transducer electrically connected to the electrical wire, whereby at least a portion of the ultrasonic transducer is positioned within the housing, and a mirror element positioned within the housing and including a mirror surface beveled at or about 45° to the axis of the multimode fiber, whereby the catheter is operable to deliver an optical wave and an ultrasonic wave collinearly from the housing and out of the aperture to obtain optical data and ultrasonic data within a mammalian luminal organ. The ultrasonic wave reflects from the distal end of the multimode fiber and the optical wave and the ultrasonic wave each reflect collinearly from the mirror surface of the mirror element and out of the aperture. The optical data and the ultrasonic data are each indicative of a plaque within the mammalian luminal organ.

Another aspect of the present disclosure includes disclosure of a method to obtain optical data and ultrasonic data within a mammalian luminal organ using a photoacoustic catheter, similar to the photoacoustic catheter described above. The method includes steps of introducing at least a portion of the photoacoustic catheter into the mammalian luminal organ, transmitting an optical wave from the multimode fiber and toward the mirror surface of the mirror element, and transmitting an ultrasonic wave from the ultrasonic transducer and toward the distal end of the multimode fiber. The method also includes redirecting the ultrasonic wave from the distal end of the multimode fiber and toward the mirror surface of the mirror element, and redirecting the optical wave and the ultrasonic wave from the mirror surface and the mirror element and collinearly from the housing and out of an aperture through the housing to obtain optical data and ultrasonic data within the mammalian luminal organ.

Another aspect of the present disclosure includes disclosure of an imaging system including a photoacoustic catheter, which is similar to that described above. The imaging system includes an optical excitation source operatively connected to the photoacoustic catheter via the multimode fiber, and a pulser/receiver operatively connected to the photoacoustic catheter via the ultrasonic transducer. The photoacoustic catheter is operable to deliver an optical wave through the multimode fiber and to deliver an ultrasonic wave collinearly from the housing and out of an aperture through the housing. The optical wave and the ultrasonic wave are detected by the ultrasonic transducer and received by the pulser/receiver. The imaging system also includes a data acquisition device operatively connected to the photoacoustic catheter via the pulser/receiver to digitize signals received at the pulser/receiver.

BRIEF DESCRIPTION OF THE DRAWINGS

The above mentioned and other features and objects of this invention, either alone or in combinations of two or more, and the manner of attaining them, will become more apparent and the invention itself will be better understood by reference to the following description of an embodiment of the invention taken in conjunction with the accompanying drawings, wherein:

FIG. 1A shows a wireframe plan view of a catheter probe in a disassembled configuration according to exemplary embodiments of the present disclosure.

FIG. 1B shows a wireframe plan view of a catheter probe in an assembled configuration according to exemplary embodiments of the present disclosure.

Figure 1C:
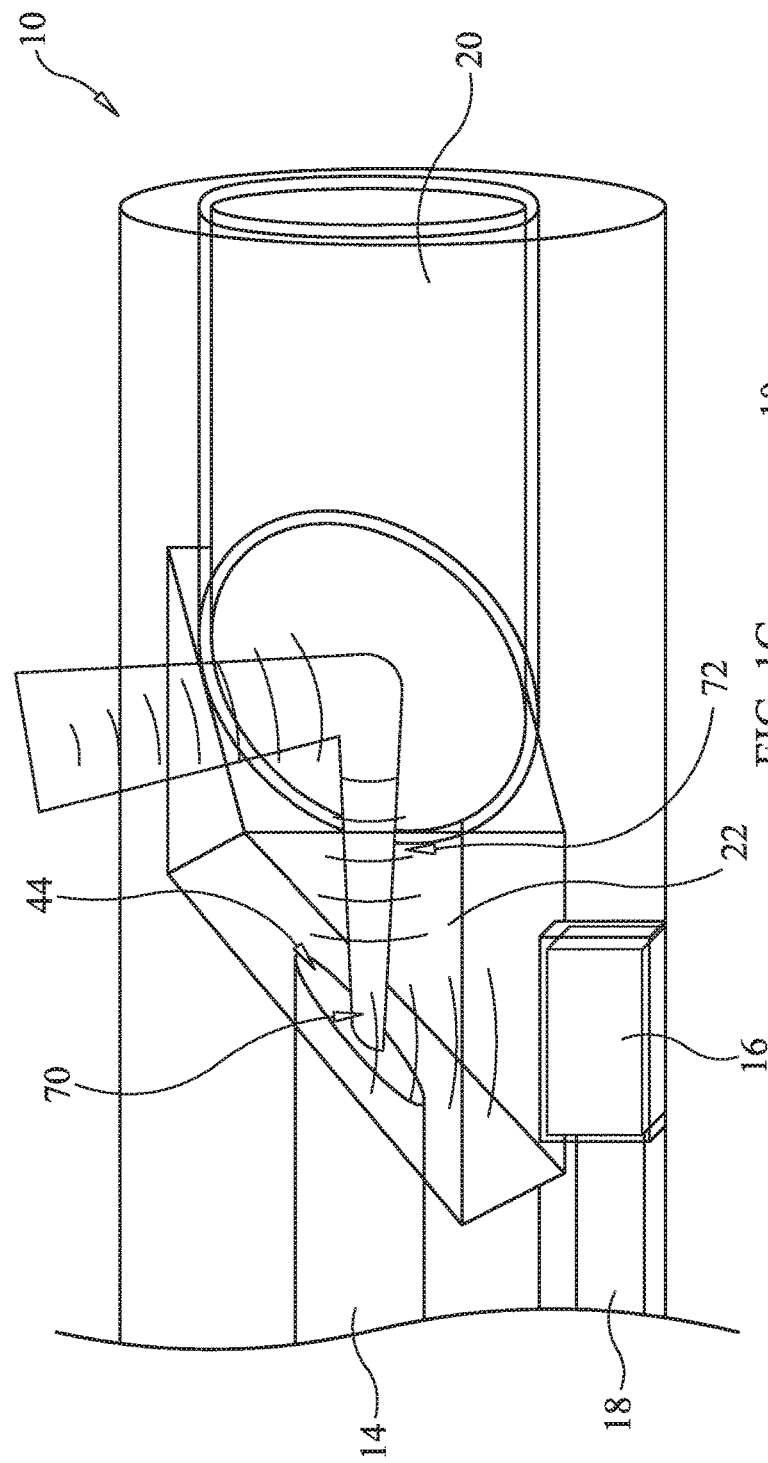
FIG. 1C shows a detail wireframe plan view of a catheter probe i n an assembled configuration according to exemplary embodiments of the present disclosure.

Corresponding reference characters indicate corresponding parts throughout the several views. Although the drawings represent embodiments of the present invention, the drawings are not necessarily to scale and certain features may be exaggerated in order to better illustrate and explain the full scope of the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is intended, with any additional alterations, modifications, and further applications of the principles of this disclosure being contemplated hereby as would normally occur to one skilled in the art. Accordingly, this disclosure is intended to cover alternatives, modifications, and equivalents as may be included within the spirit and scope of this disclosure as defined by the appended claims. While this technology may be illustrated and described in a preferred embodiment, the systems, methods, and techniques hereof may comprise many different configurations, forms, materials, and accessories.

The present disclosure includes a photoacoustic catheter probe that uses collinear alignment of optical and acoustic waves to overcome the drawbacks in aforementioned conventional IVPA catheters. In at least one embodiment, an optical beam delivered through a 365-μm-core multimode fiber (MMF) with a low numerical aperture of 0.22 enables quasi-uniform illumination along the imaging depth. An outer diameter of 1.6 mm was obtained for the catheter tip through novel arrangement of the optical and acoustic elements. The disclosed collinear catheter probe ensures an efficient overlap between optical and photoacoustic waves over a 6 mm imaging depth. The capability of the collinear catheter probe was evaluated through ex vivo high-speed IVPA imaging of a diseased porcine carotid artery and a human coronary artery, with optical excitation via a lab-built optical parametric oscillator outputting optical pulses at 1.7 μm wavelength and 500 Hz repetition rate.

A catheter probe 10, also referred to as a photoacoustic catheter, according to at least one embodiment of the present disclosure is shown in FIGS. 1A-1D. The catheter probe 10 includes a housing 12. The housing 12 includes a lumen 24 formed therethrough, a signal chamber 22 formed therein, and a transducer chamber 26 formed in or near an exterior wall of the housing 12. The housing 12 may further include a wire passage 28. The housing 12 may be fabricated by molding, casting or additive manufacturing techniques, such as a micro-resolution stereolithography process (e.g., such as practiced by Proto Labs, Inc.).

The catheter probe 10 includes a multimode fiber 14 capable of transmitting and emitting an optical wave 70 of electromagnetic energy (i.e., a light beam). The multimode fiber 14 is at least partially disposed within the lumen 24 of the housing 12. In at least one embodiment, the multimode fiber 14 may include a core/cladding diameter of 365/400 μm, NA of 0.22 (e.g., multimode fiber FG365LEC, Thorlabs, Inc.). The multimode fiber 14 includes a fiber axis 40 defined along the length of the multimode fiber 14 and a distal end 42. The distal end 42 terminates at a reflection face 44 configured at approximately a 45° angle to the fiber axis 40. The multimode fiber 14 includes a proximal end (not shown) that may terminate at an inlet face (not shown) configured at substantially a 90° angle to the fiber axis 40. The reflection face 44 and the inlet face may be polished with a fiber polisher (e.g., NANOpol, ULTRA TEC Manufacturing, Inc.). The distal end 42 of the multimode fiber 14 may be disposed within the lumen 24 of the housing 12 such that the reflection face 44 enters the signal chamber 22, as shown in FIG. 1B.

The catheter probe 10 further includes a transducer 16, also referred to as an ultrasonic transducer, disposed at least partially within the transducer chamber 26 of the housing 12 and capable of sensing acoustic waves 72 directed toward a sensing area 68 of the transducer 16. A wire 18 electrically connected to the transducer 16 may be disposed in the wire passage 28. The wire 18 enables signals from the transducer 16 to be communicated to and from an imaging system as described further herein. The transducer 16 may be any suitable ultrasonic transducer. In certain embodiments, the transducer 16 may be a single-element ultrasonic transducer having a relatively small form factor. In at least one embodiment, the transducer 16 may be a single-element ultrasonic transducer with dimensions of 0.5×0.6×0.2 mm$^3$, center frequency of 42 MHz and bandwidth of 60% (e.g., as sold by Blatek, Inc.).

Figure 1D:
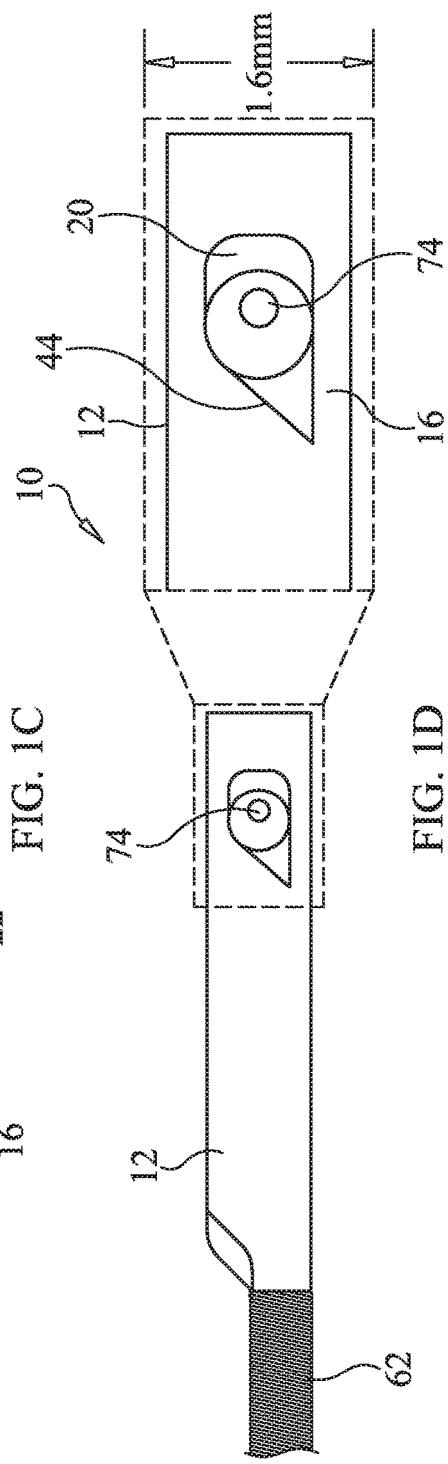
FIG. 1D shows a plan view of a catheter probe with a detail inset according to exemplary embodiments of the present disclosure.

The transducer 16 may be oriented within the transducer chamber 26 such that the sensing area 68 of the transducer 16 faces the reflection face 44 of the multimode fiber 14. The transducer 16 and the multimode fiber 14 may be positioned and oriented to ensure the collinearity between the optical wave 70 emitted from the multimode fiber 14 and the acoustic waves 72 transmitted through the catheter probe 10, as shown in FIGS. 1C and 1D. Accordingly, the refection face 44 may be positioned to lie in the acoustic reflection plane of the transducer 16. The housing 12 also includes a signal aperture 74 formed therethrough, as shown in FIG. 1D, to enable the optical wave 70 and acoustic waves 72 to be transmitted through the catheter probe 10.

The catheter probe 10 further includes a mirror element 20 disposed in a mirror passage 30 formed in a distal end of the housing 12, as shown in FIGS. 1A and 1B. As shown in FIG. 1A, the mirror element 20 includes a mirror face 66 capable of reflecting the optical wave 70 and acoustic waves 72. The mirror element 20 is positioned and oriented to ensure the optical wave 70 and acoustic waves 72 are emitted radially from the catheter probe 10, as shown in FIG. 1 C. In at least one embodiment, the mirror element 20 may be a mirror rod in which the mirror face 66 is disposed at a mirror rod distal end 64. In such an embodiment, the mirror element 20 may be a mirror rod having a diameter of I mm (e.g., as sold by Edmund Optics, Inc.). The relative positions among each of the components may be optimized by monitoring the photoacoustic signal in real time under an aqueous environment.

The catheter probe 10 may further include a torque coil 62 attached to the housing 12, as shown in FIG. 1D. The torque coil 62 may enclose the multimode fiber 14 and the wire 18 extending from the transducer 16. The catheter probe 10 may include various connectors and accessories as needed, for example, a fiber connector installed on a proximal end of the multimode fiber 14. The catheter probe 10 may further include a solution, such as an aqueous solution, disposed and contained within the signal chamber 22, where the solution is capable of transmitting the optical wave 70 and acoustic waves 72.

The multimode fiber 14 delivers the optical wave 70 to the catheter probe 10. The fiber distal end 42 of the multimode fiber 14 may be polished to 45° for reflecting the ultrasonic wave 72, while the optical wave 70 still propagates forward after the polished end when the multimode fiber 14 is submerged in an aqueous environment. The transducer 16 is disposed relative to the multimode fiber 14 such that the sensing area 68 of the transducer 16 faces the polished reflection face 44. Therefore, the optical and ultrasonic paths are collinear after encountering the reflection face 44, as shown in FIG. 1C. The 45° mirror face 66 of the mirror element 20 disposed opposite the multimode fiber 14 redirects both the optical wave 70 and ultrasonic waves 72 perpendicularly for side-view illumination and imaging. It should be noted that the ultrasound trace after the mirror element 20 is designed to be perpendicular to its receiving plane within the housing 12 to prevent direct ultrasound wave venting from the transducer 16 as shown in FIG. 1C, which may cause errant image reconstruction. The disclosed catheter probe 10 ensures that optical and acoustic waves 70 and 72 are collinear within a large tissue depth. The components involved are installed in the housing 12 having an outer diameter reasonably compatible in clinical settings, thus greatly simplifying the catheter assembly process. An embodiment of the catheter probe 10 is shown in FIG. 1D, with its outer diameter measured to be 1.6 mm.

Figure 2:
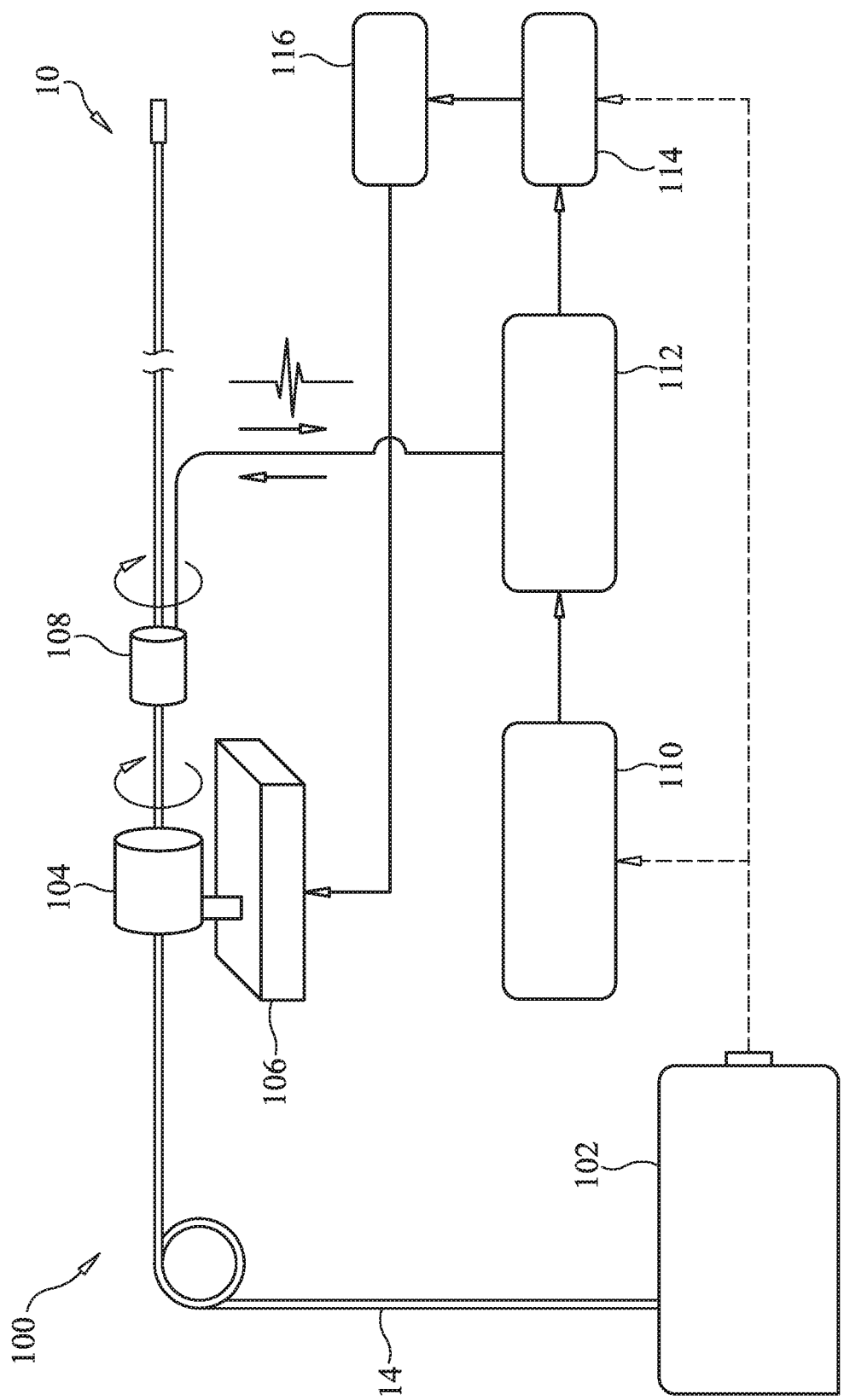
FIG. 2 shows a schematic of an imaging system according to exemplary embodiments of the present disclosure.

An imaging system 100 according to at least one embodiment of the present disclosure is shown in FIG. 2. The imaging system 100 includes the catheter probe 10 connected to an optical parametric oscillator (OPO) 102. In at least one embodiment, the OPO 102 may be a potassium titanyl phosphate (KTP)-based OPO emitting at 1.7 µm with a repetition rate of 500 Hz and pulse width of approximately 13 ns, which provides an optical excitation source for photoacoustic imaging using the imaging system 100. The pulse energy at the fiber distal end 42 of the multimode fiber 14 may be controlled to approximately 120 µJ, corresponding to an energy density of approximately 30 mJ/cm$^2$ at the tissue surface, which is below the 1.0 J/cm$^2$ ANSI safety standard for skin at 1.7 µm.

Light generated by the OPO 102 may be coupled to the catheter probe 10 via the multimode fiber 14 via an optical rotary joint 104 and a slip ring 108. The optical rotary joint 104 together with the slip ring 108 may control the rotational scanning of the catheter probe 10. The optical rotary joint 104 may be mounted to a pullback stage 106 to enable 3-D imaging.

Sequential photoacoustic and ultrasound signals may be generated and detected with a proper time delay. A trigger signal provided by a Q-switch of the OPO 102 synchronizes the data acquisition of the optical wave 70 and acoustic wave 72 signals. A time delay of approximately 10 is may be applied to an ultrasound pulser/receiver 112 via a delay generator 110. Both the optical wave 70 and acoustic wave 72 signals are sequentially detected by the transducer 16 and received by the pulser/receiver 112. A data acquisition card 114 may be used to digitize and transfer the generated signals to a computer 116, which may employ data acquisition software such as LabView® software. The imaging system 100 may include the delay generator 110 (e.g., delay generator 37000-424 from Datapulse, Inc.), the pulser/receiver 112 (e.g., pulser/receiver 5073PR from Olympus Inc.), the data acquisition card 114 (e.g., data acquisition card ATS9462 PCI express digitizer from AlazerTech, Canada), and/or the computer 16. In certain embodiments, the pulser/receiver 112 may employ an amplification factor of 39 dB, and the data acquisition card 114 may employ 16-bit digitization and a 180 MS/s sampling rate. In at least one embodiment, the imaging system 100 may have an imaging speed of approximately 1 frame per second, which is around 50 times faster than conventional IVPA imaging systems based on 10-Hz Nd:YAG lasers.

Exemplary embodiments of the catheter probe 10 and imaging system 100 were characterized for performance evaluation and validated with ex vivo artery imaging as described in the following experiments.

Experiment 1: Characteristics of Spatial Resolution and Imaging Depth

Figure 3A:
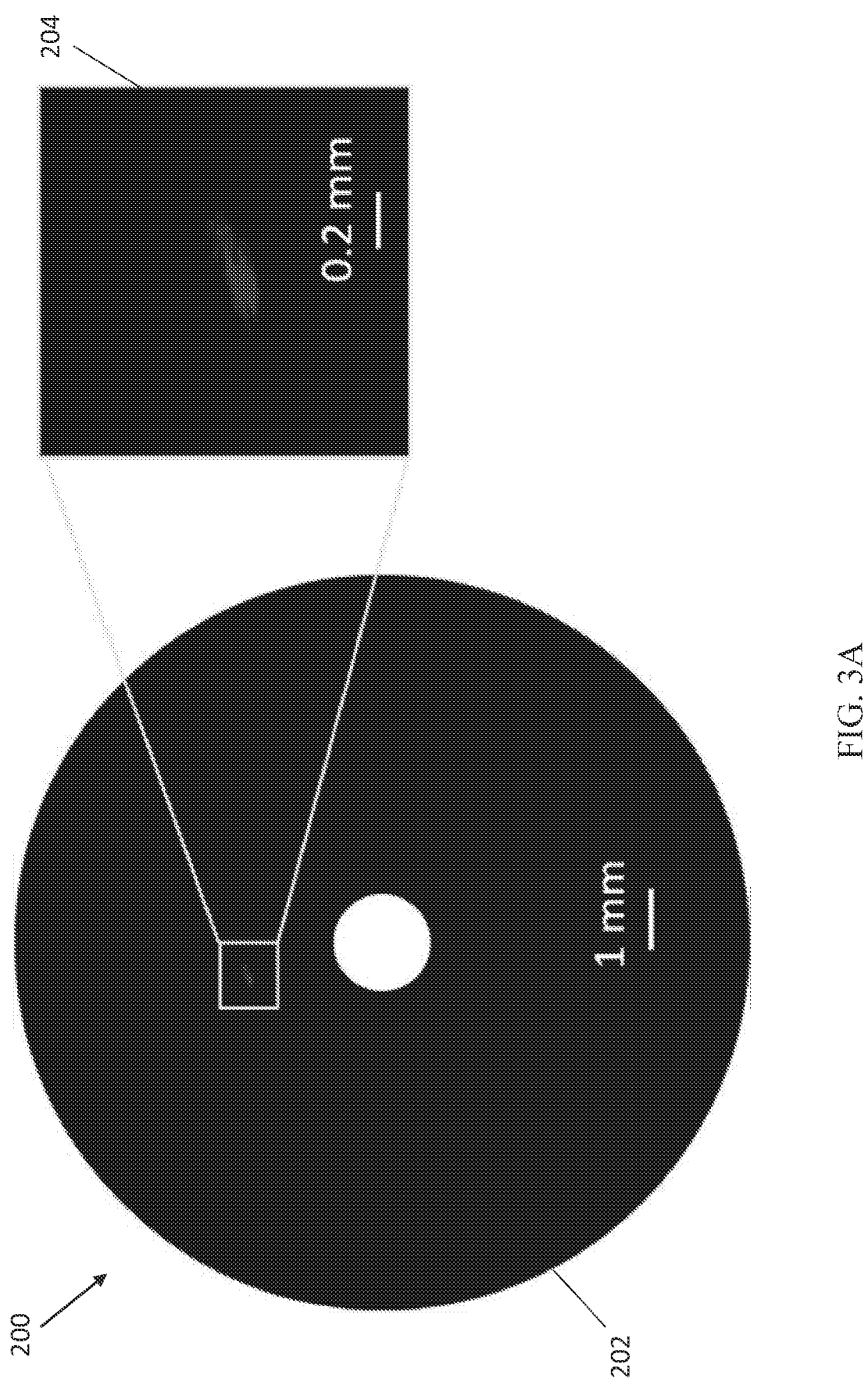
FIG. 3A shows a cross-sectional photoacoustic image with close-up inset from a catheter probe according to exemplary embodiments of the present disclosure.

The spatial resolution of an exemplary embodiment of the catheter probe 10 and the imaging system 100 was evaluated by photoacoustically imaging a carbon fiber with 7-µm diameter as a first test sample. The carbon fiber serves as a model target to determine the spatial resolution of the imaging system 100 due to its strong optical absorption and well-defined thin diameter. The carbon fiber was positioned parallel to the catheter probe 10 with a variable distance controlled by a translation stage. The experiments were performed in deuterium oxide (D20) medium because of its lower optical absorption at 1.7 µm compared to water. FIG. 3A shows a reconstructed cross-sectional photoacoustic image 200 of a carbon fiber 202 with a rotational catheter scanning. An inset 204 shows the zoom-in view of the carbon fiber image.

Figure 3C:
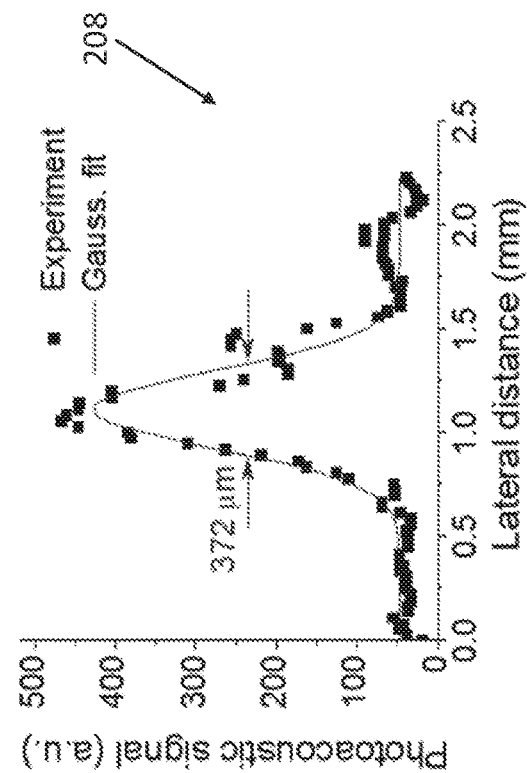
FIG. 3C shows a graphical plot of a photoacoustic signal (measured in arbitrary units) over a lateral distance (measured in millimeters) for a catheter probe according to exemplary embodiments of the present disclosure.
Figure 3B:
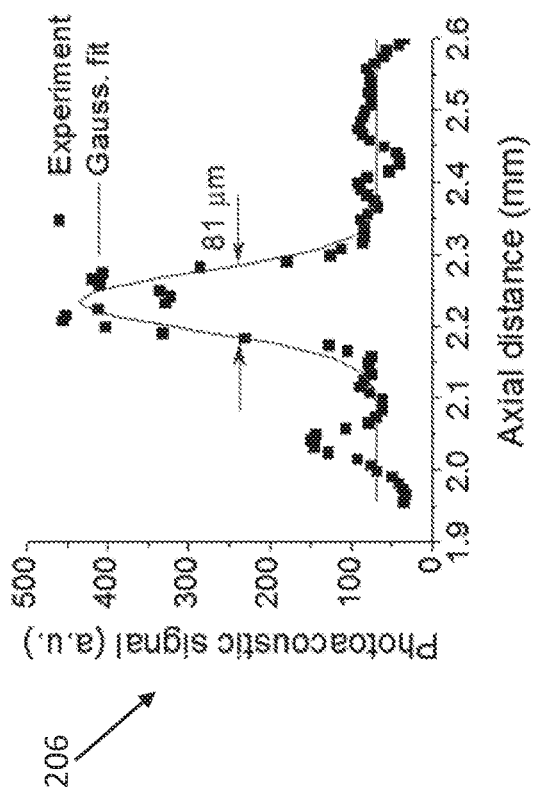
FIG. 3B shows a graphical plot of a photoacoustic signal (measured in arbitrary units) over an axial distance (measured in millimeters) for a catheter probe according to exemplary embodiments of the present disclosure.
Figure 3E:
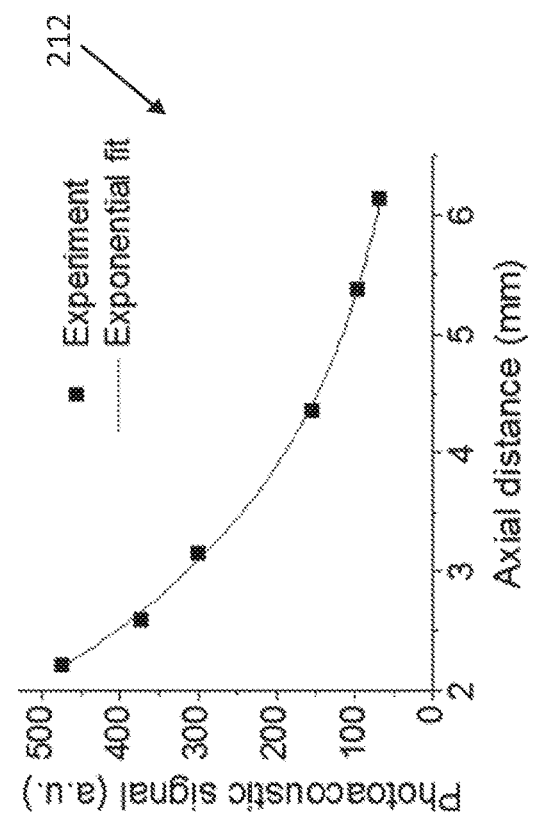
FIG. 3E shows a graphical plot of the magnitude of a photoacoustic signal (measured in arbitrary units) over an axial distance (measured in millimeters) for a catheter probe according to exemplary embodiments of the present disclosure.
Figure 3D:
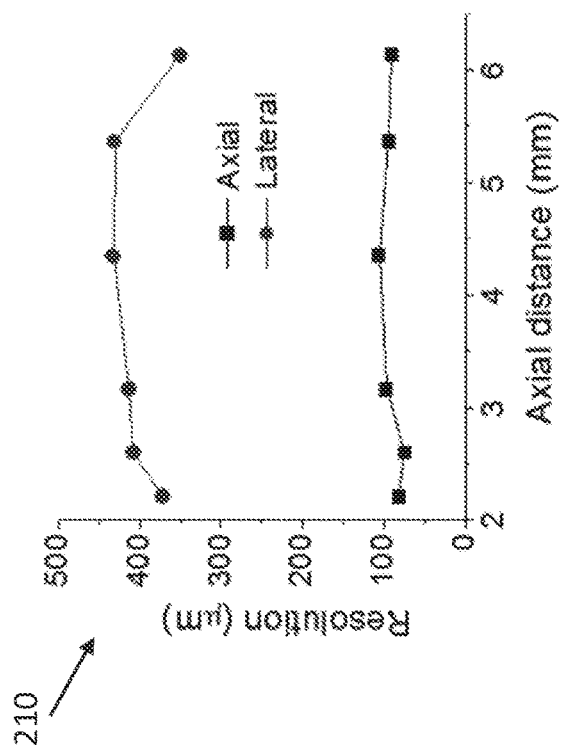
FIG. 3D shows a graphical plot of axial and lateral resolutions (measured in microns) of a photoacoustic signal over an axial distance (measured in millimeters) for a catheter probe according to exemplary embodiments of the present disclosure.

The generated photoacoustic signals along the axial and lateral directions centered at the carbon fiber position are plotted in respective graphical plots 206 and 208 of FIGS. 3B and 3C to determine the spatial resolution. The axial and lateral resolutions are derived from the full width at half maximum of Gaussian fit of these results. An axial resolution of 81 µm and lateral resolution of 372 µm were obtained at a radial distance of 2.2 mm. Spatial resolutions for photoacoustic imaging at different axial distances were obtained similarly by changing the position of the carbon fiber as displayed in a graphical plot 210 of FIG. 3D. The axial resolutions are found to fluctuate around 80 µm, which are primarily determined by the bandwidth of the transducer, while lateral resolutions are found to vary from 350 µm to 430 µm, which may be due to the non-focus property of the ultrasonic transducer. The magnitude of the photoacoustic signals at different axial distances is plotted as well in a graphical plot 212 of FIG. 3E. FIG. 3E shows an approximate exponential decay along the axial direction. Notably, the overlap range between optical beam and ultrasonic wave was found to be over 6 mm, which has not been achieved for non-collinear catheter designs previously reported. This imaging depth is sufficient for intravascular applications.

Experiment 2: Chemical Specificity Validation with a Lipid-Mimicking Phantom

A lipid-mimicking phantom comprised of a butter rod and a portion of porcine intramuscular fat were employed for photoacoustic imaging to evaluate the sensitivity and validate the chemical specificity of our system as a second test sample. Similar to pathologic lipid deposition in atherosclerosis, both butter and intramuscular fat are abundant in CH2 groups, which exhibit strong absorptions at their first overtone transitions around 1.7 µm. Porcine intramuscular fat serves as a reliable model of pathologic lipid deposition, thus validating the feasibility of our photoacoustic catheter probe to perform intravascular imaging. The second test sample was prepared from a 2.5% agarose gel made from agar powder and D20 approximately mimics the tissue environment. A butter rod with a diameter of about 1.5 mm and a small piece of intramuscular fat were embedded in the agarose gel as imaging targets. A central hole in the phantom was reserved for catheter insertion. The phantom was fully submerged in D20 during imaging experiment to ensure a lower optical loss at 1.7 μm.

Figure 4C:
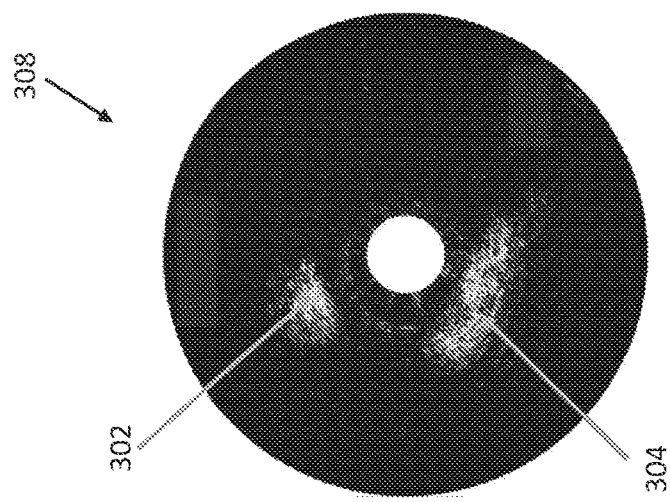
FIG. 4C shows a cross-sectional image of a photoacoustic image merged with an ultrasonic image from a catheter probe according to exemplary embodiments of the present disclosure.
Figure 4B:
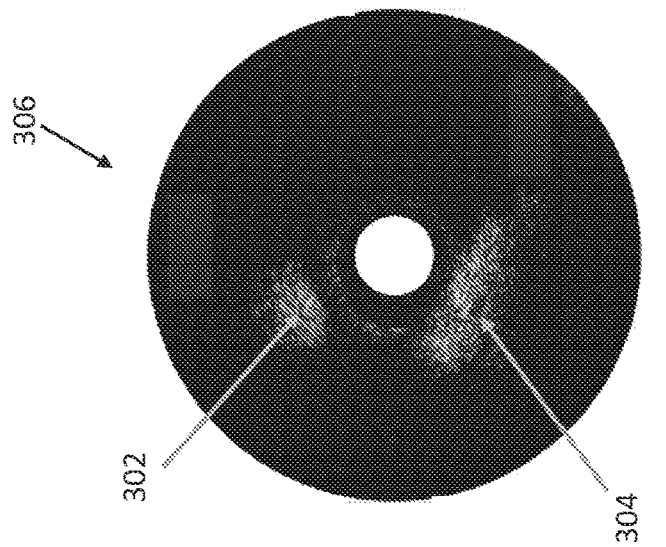
FIG. 4B shows a cross-sectional ultrasonic image from a catheter probe according to exemplary embodiments of the present disclosure.
Figure 4A:
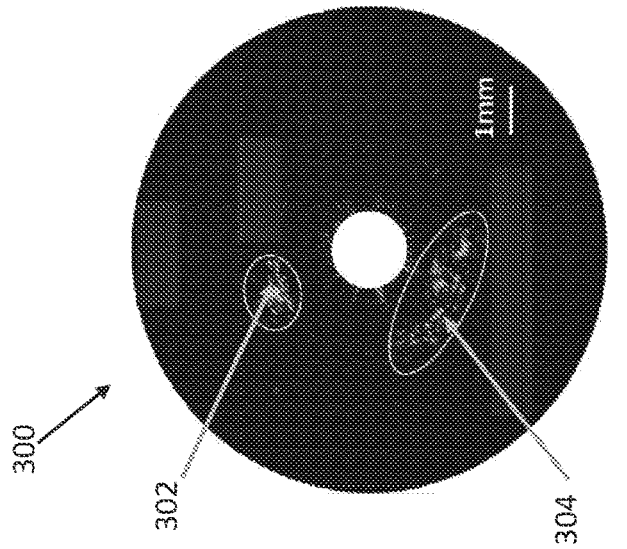
FIG. 4A shows a cross-sectional photoacoustic image, with shapes and positions of butter and fat samples of a lipid-mimicking phantom highlighted, from a catheter probe according to exemplary embodiments of the present disclosure.

Both photoacoustic and ultrasound images of the phantom are shown in respective images 300, 306, and 308 of FIGS. 4A-4C. Both butter 302 and fat 304 can be identified from both photoacoustic and ultrasound images, with strong association between them on position and morphology, as highlighted in FIG. 4A. The signal-to-noise ratios for butter and fat in photoacoustic image were calculated to be 38 and 18, respectively, while the signal-to-noise ratios are 30 and 46 for butter and fat in ultrasound mode. The photoacoustic signals are specific for the density of CH2 bond in these two targets, while the ultrasound signals are related to the overall structural properties. These results from the lipid-mimicking phantom presented in FIGS. 4A-4C validate the performance of photoacoustic and ultrasonic imaging of lipid using the catheter probe 10, indicating the imaging system 100 can be used for reliable IVPA and IVUS imaging of an artery.

Experiment 3: IVPA Imaging of Lipid-Laden Carotid Artery Excised from Ossabaw Swine The performance of our IVPA imaging system was validated by ex vivo imaging of a diseased porcine carotid artery. The porcine atherosclerotic carotid artery was harvested from a miniature Ossabaw swine and fixed in 10% formalin. A segment of artery with suspected plaque was selected and cut as a region of interest with the aid of a microscope. The artery segment was then held by agarose gel and submerged under D20 for imaging experiment.

Figure 5C:
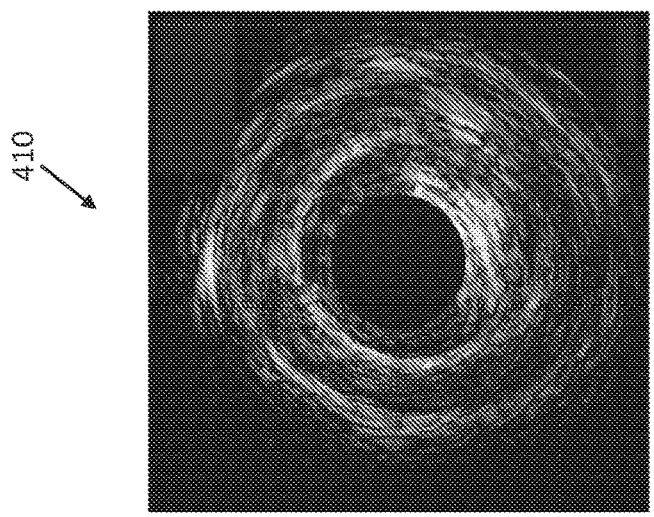
FIG. 5C shows a cross-sectional image of a photoacoustic image merged with an ultrasonic image from a catheter probe according to exemplary embodiments of the present disclosure.
Figure 5B:
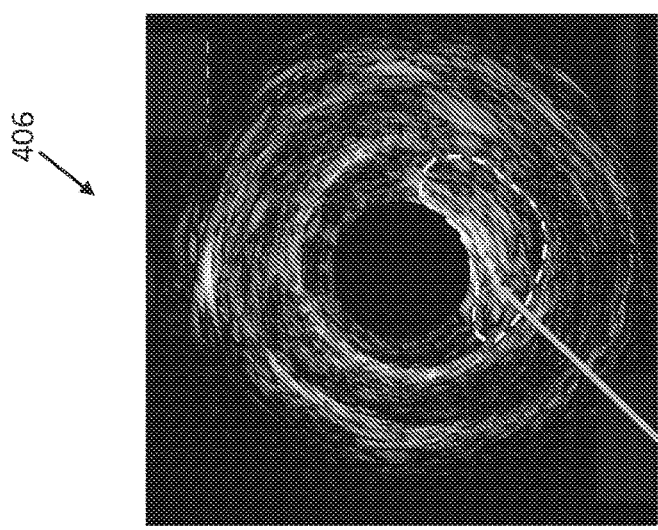
FIG. 5B shows a cross-sectional ultrasonic image, with lipid deposition highlighted, from a catheter probe according to exemplary embodiments of the present disclosure.
Figure 5A:
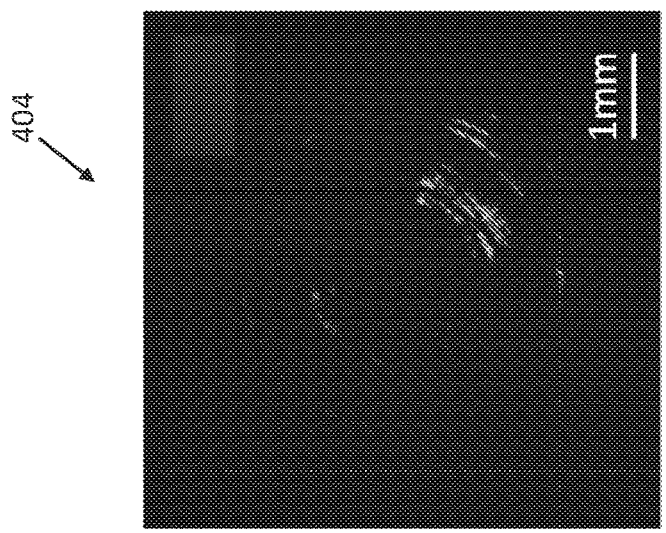
FIG. 5A shows a cross-sectional photoacoustic image from a catheter probe according to exemplary embodiments of the present disclosure.
Figure 5E:
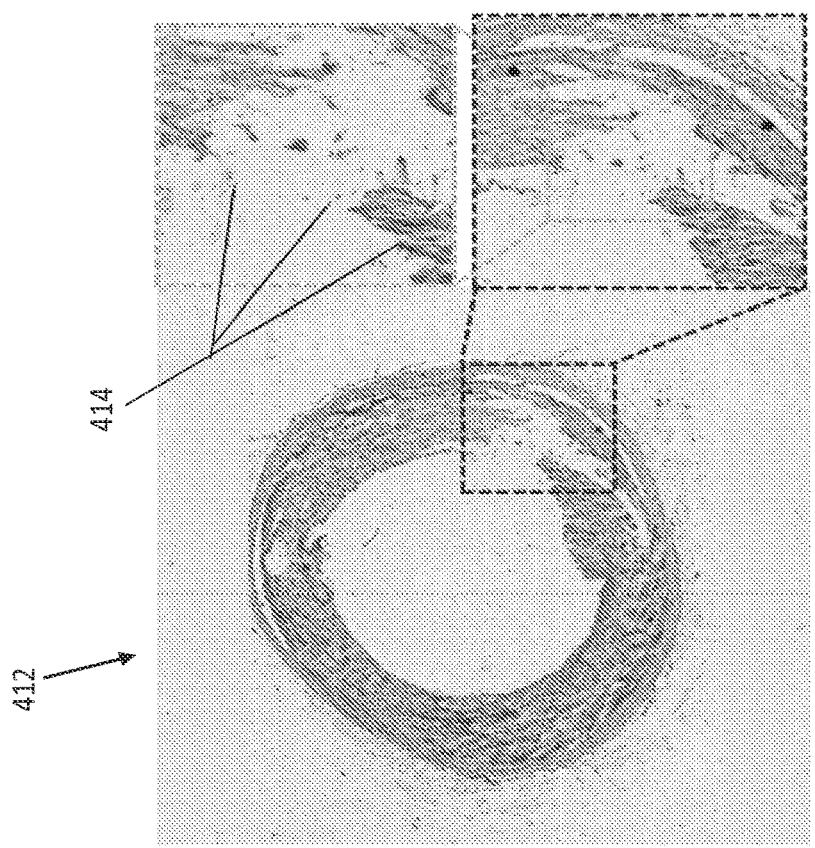
FIG. 5E shows a histology with close-up insets of an artery segment used to demonstrate a catheter probe according to exemplary embodiments of the present disclosure.
Figure 5D:
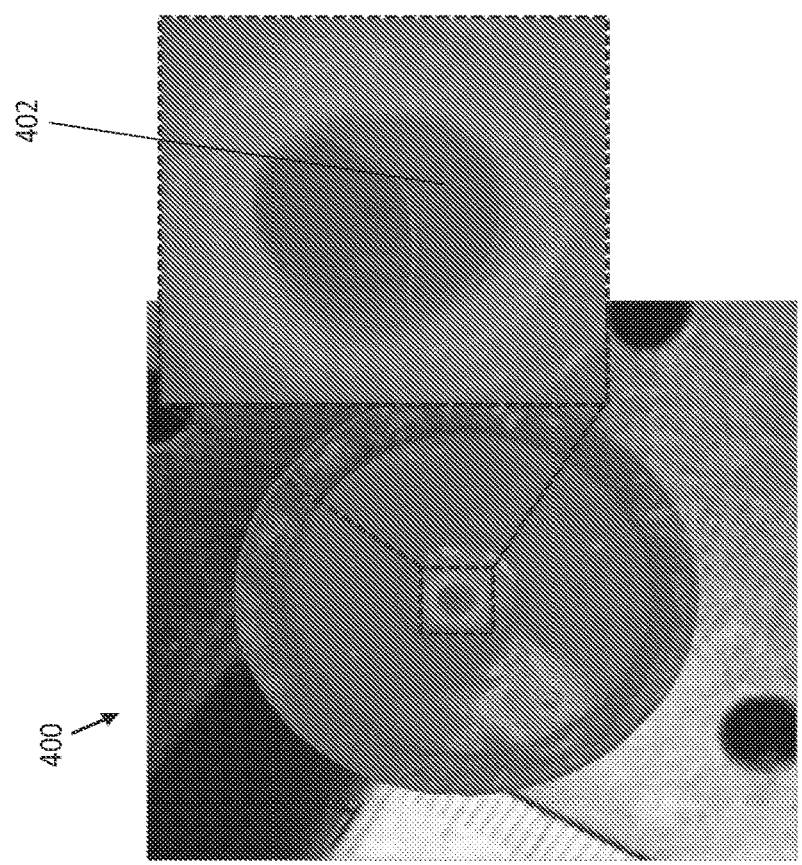
FIG. 5D shows a cross-sectional photograph with a close-up inset of an artery segment used to demonstrate a catheter probe according to exemplary embodiments of the present disclosure.

A segment of the artery with suspected plaque (shown as artery stenosis 402 in a cross-sectional photograph 400 FIG. 5D) was selected as the imaging target. Co-registered and merged IVPA/IVUS images 404, 406, and 410 were obtained as shown in FIGS. 5A-5C. From the IVUS image 406 in FIG. 5B, the characteristic three-layer appearance and luminal area of the carotid artery can be visualized, with the suspected plaque region 408 and inner and outer boundaries of the artery inscribed, which agree well with gross inspection at the plaque position (see FIG. 5D). Strong photoacoustic signal within the plaque region shown in FIG. 5A indicates a possible lipid-rich core of the plaque. The merged image 410 in FIG. 5C shows the overlap between the photoacoustic and ultrasonic signal at the plaque area. The imaged cross-sectional region was further sectioned and stained for histology, as shown in a histology 412 of FIG. 5E. The lumen size and arterial structure were verified by the histology. The plaque position was highlighted in the detailed section inset. The lipid deposition, which might have been leached out during the histology process, is suggested by the blank area. Some debris of the lipid core can still be visualized in the zoom-in view indicated by black lines at 414.

Experiment 4: IVPA Imaging of Fresh Coronary Artery Excised from Human Patient

The performance of the catheter probe 10 and the imaging system 100 were further validated by ex vivo imaging a perfused fresh right coronary artery from a human patient. The fresh right coronary artery was harvested from an explanted human heart at the time of transplant. The vessel segment was excised from the ostium to 6 cm distally, leaving approximately 5 mm of surrounding perivascular fat attached. The ostium was cannulated with an 8F introducer sheath and side branches were ligated to allow for pressure perfusion. The artery was then pinned in a Sylgard® 184 Silicone Elastomer tray, submerged in phosphate-buffered saline at room temperature, and perfused to mimic physiologic pressure during imaging.

Figure 6A:
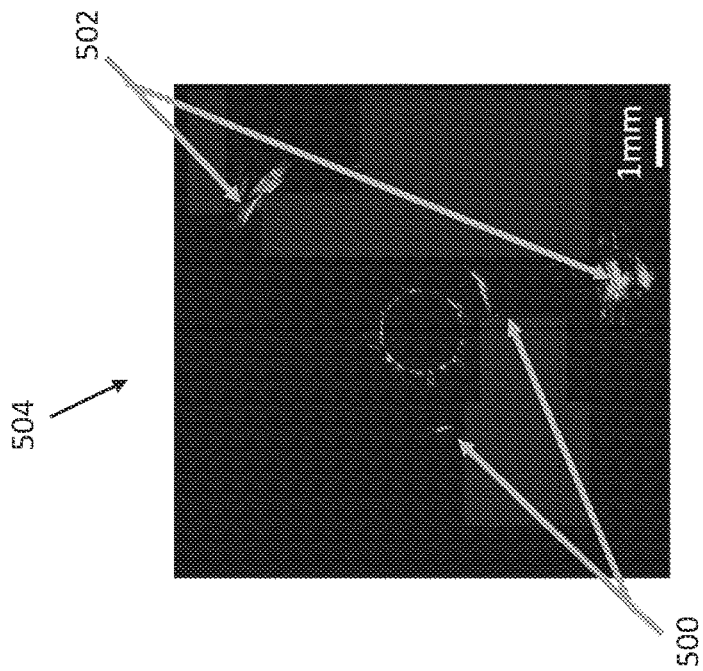
FIG. 6A shows a cross-sectional photoacoustic image, with shapes and positions of lipid and periadventitial fat deposits highlighted, from a catheter probe according to exemplary embodiments of the present disclosure.
Figure 6B:
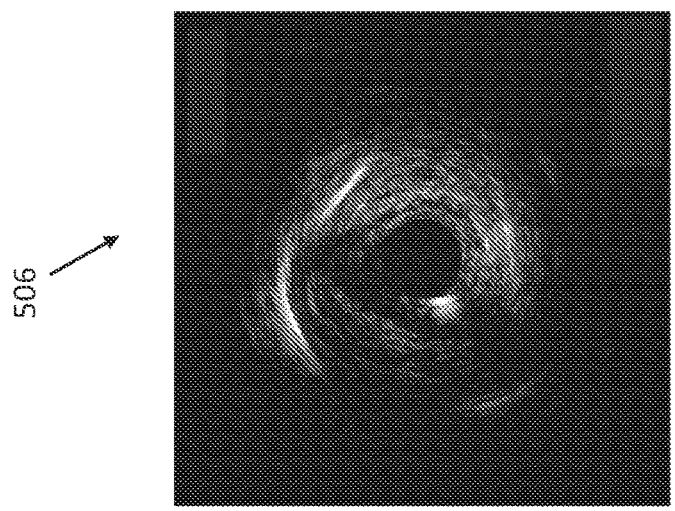
FIG. 6B shows a cross-sectional ultrasonic image from a catheter probe according to exemplary embodiments of the present disclosure.
Figure 6C:
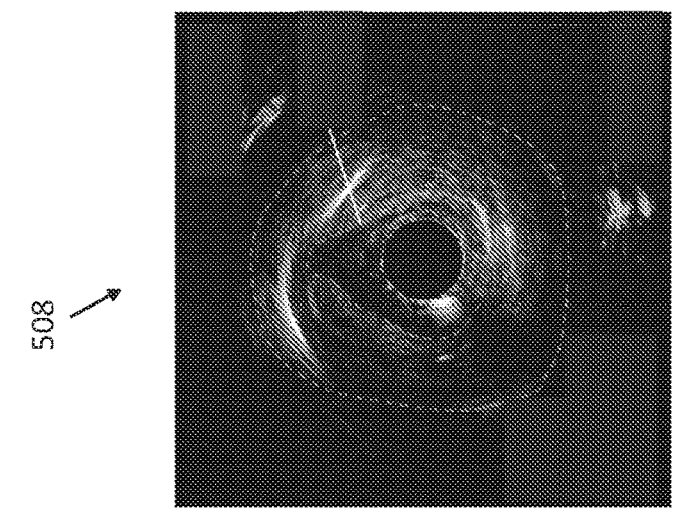
FIG. 6C shows a cross-sectional image of a photoacoustic image merged with an ultrasonic image with an outer boundary and lumen of an artery highlighted, from a catheter probe according to exemplary embodiments of the present disclosure.

The artery segment was imaged in 3-D using the optical rotary joint 104 and a linear pullback stage 106. At a particular longitudinal position, a region of interest was identified with a strong photoacoustic signal in the arterial wall, which could possibly indicate lipid depositions 500 as shown in respective images 504, 506, and 508 of FIGS. 6A-6C. Furthermore, an intense photoacoustic signal peripheral from the vessel wall with an imaging depth of 4.3 mm was observed, suggesting that the imaging system 100 is able to penetrate through the entire arterial wall to reach surrounding perivascular fat 502 that was retained on the excised vessel.

In the experiments described herein, the catheter probe 10 and imaging system 100 demonstrated greatly improved overlap between optical and acoustic waves. The catheter probe 10 and imaging system 100 provided optimal photoacoustic sensitivity over an imaging depth over 6 mm, allowing reliable access of the deeper component information in the entire arterial wall, including perivascular fat. Even so, the photoacoustic signal along an A-line still decayed exponentially as shown in FIG. 3E. This decay may be affected by a number of factors including optical beam divergence, optical absorption/scattering in imaging environment, acoustic loss in medium, and unfocused transducer. Some approaches to reduce signal decay include integrating a gradient-index lens in the catheter to improve the optical beam focusing, introducing a n external wavefront shaping method to focus the light beam deeper inside the tissue, and using a quasi-focused transducer to enhance the acoustic receiving efficiency.

In at least one embodiment of the present disclosure, the diameter of the catheter probe 10 is 1.6 mm, which is affected by the size of the mirror element 20 (i.e., rod mirror having a 1 mm diameter). In certain embodiments, the mirror element 20 may have a reduced diameter of 0.5 mm (e.g., using a rod mirror with a 0.5 mm diameter). In such an embodiment, the catheter probe 10 may be further reduced to about 1 mm in diameter, which is similar to the size of certain conventional commercially available IVUS catheter probes.

In at least one embodiment of the present disclosure, the imaging speed of the imaging system 100 is 1 frame per second, which is based on the 500 Hz repetition rate of the OPO 102 and one revolution per second rotation speed of the catheter probe 10. Considering the lateral resolution of approximately 425 μm at an axial distance of 5 mm, the number of A-lines for each cross-sectional image may be reduced to 75, which would enable a maximum imaging speed over 6 frames per second. In certain embodiments, the OPO 102 includes a laser system having a higher repetition rate of 2 kHz, which further improves the imaging speed of the imaging system 100 to approach that of conventional commercial in vivo intravascular imaging systems.

The present disclosure includes a miniature IVPA catheter probe with collinear overlap between the optical and acoustic fields. The catheter probe enables high-quality IVPA imaging of the entire artery wall from lumen to perivascular fat. A lab-fabricated collinear photoacoustic catheter was evaluated for spatial resolution characterization with a 7-μm carbon fiber and chemical composition validation by using a lipid-mimicking phantom. The axial and lateral resolutions were found to be around 80 μm and 400 μm, respectively, over an imaging depth larger than 6 mm. With a co-registered IVPA/IVUS imaging system based on a lab-built 500 Hz OPO at 1.7 µm, the catheter probe was used to image a diseased carotid artery and a human coronary artery ex vivo, resulting in IVPA/IVUS images showing a lipid-rich plaque that corresponds with gross inspection.

While various embodiments of the present disclosure have been described as having an illustrative design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A photoacoustic catheter, including: an elongated catheter body having a lumen defined therethrough and a housing positioned at or near a distal end of the elongated catheter body, the housing defining an aperture therethrough;
    a length of multimode fiber extending through at least part of the lumen of the elongated catheter body, the multimode fiber having an axis along its length, whereby a distal end of the multimode fiber is beveled at or about 45° to the axis and is located within the housing;
    an electrical wire extending along the elongated catheter body;
    an ultrasonic transducer electrically connected to the electrical wire, whereby at least a portion of the ultrasonic transducer is positioned within the housing;
    and a mirror element positioned within the housing and including a mirror surface beveled at or about 45° to the axis of the multimode fiber;
    whereby the ultrasonic transducer transmits an ultrasonic wave toward the distal end of the multimode fiber and the distal end of the multimode fiber redirects the ultrasonic wave toward the mirror surface of the mirror element,
    wherein the multimode fiber transmits an optical wave toward the mirror surface of the mirror element, and both the optical wave and the ultrasonic wave each reflect collinearly from the mirror surface of the mirror element and out of the aperture to obtain optical data and ultrasonic data within a mammalian luminal organ.

2. The photoacoustic catheter of claim 1, wherein the optical data and the ultrasonic data are each indicative of a plaque within the mammalian luminal organ.

3. The photoacoustic catheter of claim 1, wherein the housing includes a signal chamber formed therein, wherein the signal chamber houses a reflection face of the multimode fiber, a sensing area of the ultrasonic transducer, and the mirror surface of the mirror element.

4. The photoacoustic catheter of claim 3, wherein the sensing area of the ultrasonic transducer faces the reflection face of the multimode fiber.

5. The photoacoustic catheter of claim 4, wherein the sensing area of the ultrasonic transducer lies in a plane substantially perpendicular to the mirror surface of the mirror element.

6. The photoacoustic catheter of claim 1, wherein a diameter of the photoacoustic catheter is approximately 1.6 mm or less.

7. The photoacoustic catheter of claim 1, wherein the ultrasonic transducer is a single element ultrasonic transducer.

8. A method of obtaining optical data and ultrasonic data within a mammalian luminal organ using a photoacoustic catheter, the photoacoustic catheter including an elongated catheter body and a housing positioned near a distal end of the elongated catheter body,
    a length of multimode fiber extending through the elongated catheter body and terminating in the housing, an ultrasonic transducer positioned at least partially within the housing,
    and a mirror element positioned at least partially within the housing and including a mirror surface, the method including steps of:
    introducing at least a portion of the photoacoustic catheter into the mammalian luminal organ;
    transmitting an optical wave from the multimode fiber and toward the mirror surface of the mirror element;
    transmitting an ultrasonic wave from the ultrasonic transducer and toward a distal end of the multimode fiber;
    redirecting the ultrasonic wave from the distal end of the multimode fiber and toward the mirror surface of the mirror element; and
    redirecting the optical wave and the ultrasonic wave from the mirror surface and collinearly from the housing and out of an aperture through the housing to obtain the optical data and the ultrasonic data within the mammalian luminal organ.

9. The method of claim 8, wherein the step of redirecting the ultrasonic wave includes redirecting the ultrasonic wave from the distal end of the multimode fiber, wherein the distal end is beveled at or about 45° to a longitudinal axis of the multimode fiber.

10. The method of claim 9, wherein the step of redirecting the optical wave and the ultrasonic wave from the mirror surface of the mirror element includes redirecting the optical wave and the ultrasonic wave from the mirror surface, wherein the mirror surface is beveled at or about 45° to the longitudinal axis of the multimode fiber.

11. The method of claim 8, wherein the step of transmitting the ultrasonic wave from the ultrasonic transducer includes transmitting the ultrasonic wave from a single-element ultrasonic transducer.

12. The method of claim 8, further including:
    receiving photoacoustic signals at a sensing area of the ultrasonic transducer.

13. The method of claim 8, further including:
    displaying an image indicative of the optical data and the ultrasonic data on a display, whereby the image simultaneously identifies a portion of the mammalian luminal organ based upon the optical data and the ultrasonic data.

14. The method of claim 13, wherein the optical data and the ultrasonic data are each indicative of a plaque within the mammalian luminal organ.

15. An imaging system including a photoacoustic catheter, the photoacoustic catheter including an elongated catheter body and a housing positioned near a distal end of the elongated catheter body, a length of multimode fiber extending through the elongated catheter body and terminating in the housing, an ultrasonic transducer positioned at least partially within the housing, and a mirror element positioned at least partially within the housing and including a mirror surface, the imaging system including:
- an optical excitation source operatively connected to the photoacoustic catheter via the multimode fiber to deliver an optical wave;
- a pulser/receiver operatively connected to the photoacoustic catheter via the ultrasonic transducer to deliver an ultrasonic wave, wherein the ultrasonic wave is delivered from the ultrasonic transducer to a distal end of the multimode fiber, and the ultrasonic wave is redirected from the distal end of the multimode fiber to the mirror surface of the mirror element;
- whereby the photoacoustic catheter delivers the optical wave and the ultrasonic wave collinearly through the housing and the optical wave and the ultrasonic wave are redirected from the mirror surface of the mirror element out of the aperture to obtain optical data and ultrasonic data within a mammalian luminal organ;
- whereby a signal from the optical wave and a signal from the ultrasonic wave are detected by the ultrasonic transducer and received by the pulser/receiver; and
- a data acquisition device operatively connected to the photoacoustic catheter via the pulser/receiver to digitize the signals received at the pulser/receiver.

16. The imaging system of claim 15, further including a computer operatively connected to the data acquisition device to display the optical data and the ultrasonic data based on the optical wave and the ultrasonic wave.

17. The imaging system of claim 15, wherein the optical excitation source is a potassium titanyl phosphate based optical parametric oscillator.

18. The imaging system of claim 15, wherein the optical excitation source is coupled to the photoacoustic catheter via the multimode fiber via an optical rotary joint and a slip ring.

19. The imaging system of claim 15, further including a trigger signal of a Q-switch of the optical excitation source synchronizing data acquisition of the signal from the optical wave and the signal from the ultrasonic wave.

* * * * *